(12) United States Patent
Saint Clair et al.

(10) Patent No.: US 9,167,972 B2
(45) Date of Patent: Oct. 27, 2015

(54) SYSTEMS AND METHODS FOR NON-CONTACT BIOMETRIC SENSING

(71) Applicant: The Boeing Company, Seal Beach, CA (US)

(72) Inventors: Jonathan Martin Saint Clair, Seattle, WA (US); David C. Soreide, Seattle, WA (US); Robert P. Higgins, Seattle, WA (US); Gary A. Ray, Issaquah, WA (US); Tyler M. Anderson, Kent, WA (US); Donald Allen Spurgeon, Port Orchard, WA (US); Mitchell D. Voth, Lake Tapps, WA (US); Paul F. Sjoholm, Renton, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/914,743

(22) Filed: Jun. 11, 2013

(65) Prior Publication Data

US 2013/0271590 A1     Oct. 17, 2013

Related U.S. Application Data

(62) Division of application No. 12/700,282, filed on Feb. 4, 2010, now Pat. No. 8,483,806.

(51) Int. Cl.
*A61B 5/0402* (2006.01)
*A61B 5/0205* (2006.01)
(Continued)

(52) U.S. Cl.
CPC ............... *A61B 5/0205* (2013.01); *A61B 5/015* (2013.01); *A61B 5/02055* (2013.01); *A61B 5/1114* (2013.01); *A61B 5/1126* (2013.01); *A61B 2560/0431* (2013.01)

(58) Field of Classification Search
CPC .. G02B 19/0085; G02B 19/009; G02B 26/10; G02B 27/48; G01H 9/00; A61B 5/015
See application file for complete search history.

(56) References Cited

U.S. PATENT DOCUMENTS

| 4,818,101 A | 4/1989 | Soreide et al. |
| 6,600,946 B1 | 7/2003 | Rice |

(Continued)

FOREIGN PATENT DOCUMENTS

EP     1434031 A2     3/2004

OTHER PUBLICATIONS

Zhu et al., Integration of Laser Vibrometry with Infrared Video for Multimedia Surveillance Display, AFRL/HECB Grant Final Performance Report; dated Dec. 1, 2004, The City College of New York, pp. 38.

(Continued)

*Primary Examiner* — Elmer Chao
(74) *Attorney, Agent, or Firm* — Armstrong Teasdale LLP (57) ABSTRACT

A non-contact biometric sensing device is described. The device includes a processing device, a user interface communicatively coupled to the processing device, a display communicatively coupled to the processing device, a laser doppler vibrometer sensor communicatively coupled to the processing device, and an infrared camera communicatively coupled to the processing device. The processing device is programmed to utilize mechanical motion data received from the laser doppler vibrometer sensor and thermal distributions data from the infrared camera to calculate biometric data, when signals originating from the laser doppler vibrometer sensor and the infrared camera are reflected back towards the device from a target.

12 Claims, 11 Drawing Sheets

(51) Int. Cl.
*A61B 5/01* (2006.01)
*A61B 5/11* (2006.01)

(56) References Cited

U.S. PATENT DOCUMENTS

| | | |
|---|---|---|
| 7,278,975 B2 | 10/2007 | McCamish et al. |
| 7,388,971 B2 | 6/2008 | Rice et al. |
| 7,539,083 B2 | 5/2009 | Blackmon et al. |
| 2003/0135097 A1* | 7/2003 | Wiederhold et al. .......... 600/301 |
| 2004/0089812 A1 | 5/2004 | Favro et al. |
| 2006/0159440 A1 | 7/2006 | Purkayastha et al. |
| 2007/0229929 A1 | 10/2007 | Soreide et al. |
| 2008/0045847 A1* | 2/2008 | Farag et al. ................... 600/500 |
| 2008/0077019 A1 | 3/2008 | Xiao et al. |
| 2008/0084385 A1 | 4/2008 | Ranta et al. |
| 2008/0314155 A1 | 12/2008 | Blackmon et al. |
| 2009/0219507 A1 | 9/2009 | Soreide et al. |

OTHER PUBLICATIONS

Morbiducci et al, Optical Vibrocardiography: A Novel Tool for the Optical Monitoring of Cardic Activity; Annals of Biomedical Engineering, dated Nov. 3, 2006, vol. 35, No. 1, pp. 45-58.

Head et al., Infrared Imaging: Making Progress in Fulfilling Its Medical Promise, IEEE Engineering in Medicine and Biology, dated Nov./Dec. 2002. pp. 80-85.

International Search Report and Written Opinion of PCT/US2010/049594; Feb. 9, 2011; 14 pages.

* cited by examiner

SYSTEMS AND METHODS FOR NON-CONTACT BIOMETRIC SENSING

STATEMENT REGARDING FEDERALLY SPONSORED RESEARCH & DEVELOPMENT

The United States Government has acquired certain rights in the invention pursuant to Contract No. W91CRB-08-C-0056, issued by the Department of Defense.

CROSS-REFERENCE TO RELATED APPLICATION

This application is a divisional application of U.S. patent application Ser. No. 12/100,282, filed Feb. 4, 2010, which is hereby incorporated by reference in its entirety.

BACKGROUND

The field of the disclosure relates generally to emergency response situations and more specifically, to methods and systems for non-contact biometric sensing.

In emergency response to disasters of various kinds, first responders are hampered by being unable to reach victims, or are encased in protective equipment that prevents sufficient contact with victims to do standard medical triage. No solution currently exists which permits noncontact standoff measurement of human vital signs. Existing solutions require contact with the victim, for example, palpating the neck or wrist of victim to measure pulse rate or respiration and/or listening for a heart beat with an ear pressed against a chest. As can be seen from the preceding description, existing triage techniques require contact. As a result triage cannot be done when contact is prevented by lack of access or when intervening materials (e.g., biohazards) hamper contact.

BRIEF DESCRIPTION

In one aspect, a non-contact biometric sensing device is provided. The device includes a processing device, a user interface, a display, a laser doppler vibrometer sensor, and an infrared camera all communicatively coupled to the processing device. The processing device is programmed to utilize mechanical motion data received from the laser doppler vibrometer sensor and thermal distributions data from the infrared camera to calculate biometric data, when signals originating from the laser doppler vibrometer sensor and the infrared camera are reflected back towards the sensing device from a target.

In another aspect, a method for sensing biometric parameters associated with an object, without contacting the object, is provided. The method includes directing a plurality of visible laser beams, emanating from a sensing device, onto the object to provide an aiming function, causing a signal from a laser doppler vibrometer sensor, the signal emanating from the sensing device, to impinge the object in the vicinity of the visible laser beams, receiving infrared data from the object at an infrared camera associated with the sensing device, the infrared data in the vicinity of the visible laser beams, and utilizing mechanical motion data associated with the object as sensed by the laser doppler vibrometer sensor and thermal distribution data as sensed by the infrared camera to calculate biometric data associated with the object.

In still another aspect, a non-contact biometric sensing device is provided. The sensing device includes a plurality of ranging lasers each configured to emanate a visible laser beam, oriented such that the visible laser beams converge at a point distant from the sensing device, thereby enabling the laser beams to be operable in aiming the sensing device at a target object. The sensing device further includes a laser doppler vibrometer sensor configured to sense mechanical motion associated with the target object, an infrared camera configured to sense thermal distribution data associated with the target object, and a visible light camera operable to obtain an image of the target object that includes the visible laser beams. The sensing device is programmed to determine a distance to the target object based upon a distance between the visible beams and further operable to use the determined distance to the target to focus the laser doppler vibrometer sensor, the infrared camera, and the visible light camera on the target object.

The features, functions, and advantages that have been discussed can be achieved independently in various embodiments or may be combined in yet other embodiments further details of which can be seen with reference to the following description and drawings.

DETAILED DESCRIPTION

Figure 1:
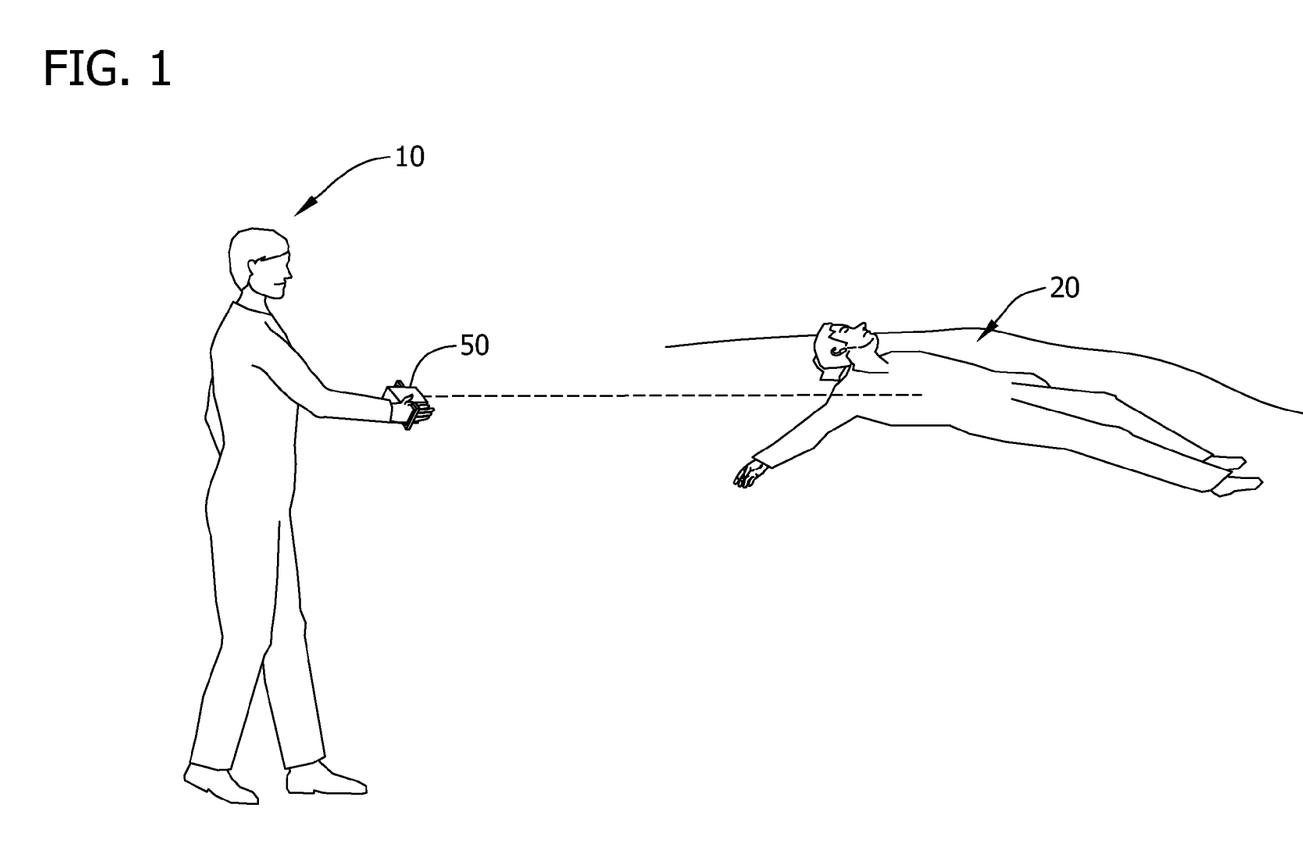
FIG. 1 is a depiction of a person using one embodiment of a remote biometric measuring device to measure vital signs of another person.

The described embodiments include a handheld emergency response triage device, for example, to assist in the on-scene assessment of victim status, via standoff assessment of key physiological parameters, the device usable by personnel wearing PPE. In embodiments, the device combine a laser Doppler vibrometry sensor with an infrared imaging device, to measure human biometric signals without contact, and with a standoff distance between the user and the person whose biometric signals are being measured. As further described, other embodiments include other non-contact physiological measuring methods and devices. FIG. 1 depicts such a device in one contemplated use. More specifically, FIG. 1 depicts a first responder 10 to an emergency situation. The circumstances and types of such emergency situations are nearly unlimited, therefore, for purposes of this disclosure, the description utilizes the example of a chemical spill or leak. Embodiments of the described device allow for the evaluation of the physical condition of accident victims remotely, safely, and accurately, minimizing the risk to first responders.

In such situations, the first responder will generally be wearing some type of personal protection equipment (PPE) that prevents him from physically contacting a person 20 that has been compromised by the emergency situation. The emergency situation may be of a nature where physical contact between the first responder 10 and the person is hazardous to the first responder 10. To address the triage needs of person 20, the first responder 10 is equipped with a non-contact biometric sensing device 50.

Non-contact biometric sensing device 50, in various embodiments, allows the first responder 10 to measure the physiological parameters of person 20. The measured physiological parameters provide the first responder 10 with indicators of physical condition of person 20, for example, by measuring mechanical motion with a laser and thermal distributions with an infrared camera. In such embodiments, the laser is able to measure mechanical motion at the surface of the skin of person 20, due to respiration and heart beat. As shown in FIG. 1, some embodiments of non-contact biometric sensing device 50 are handheld devices. Other portable configurations are contemplated.

Figure 2:
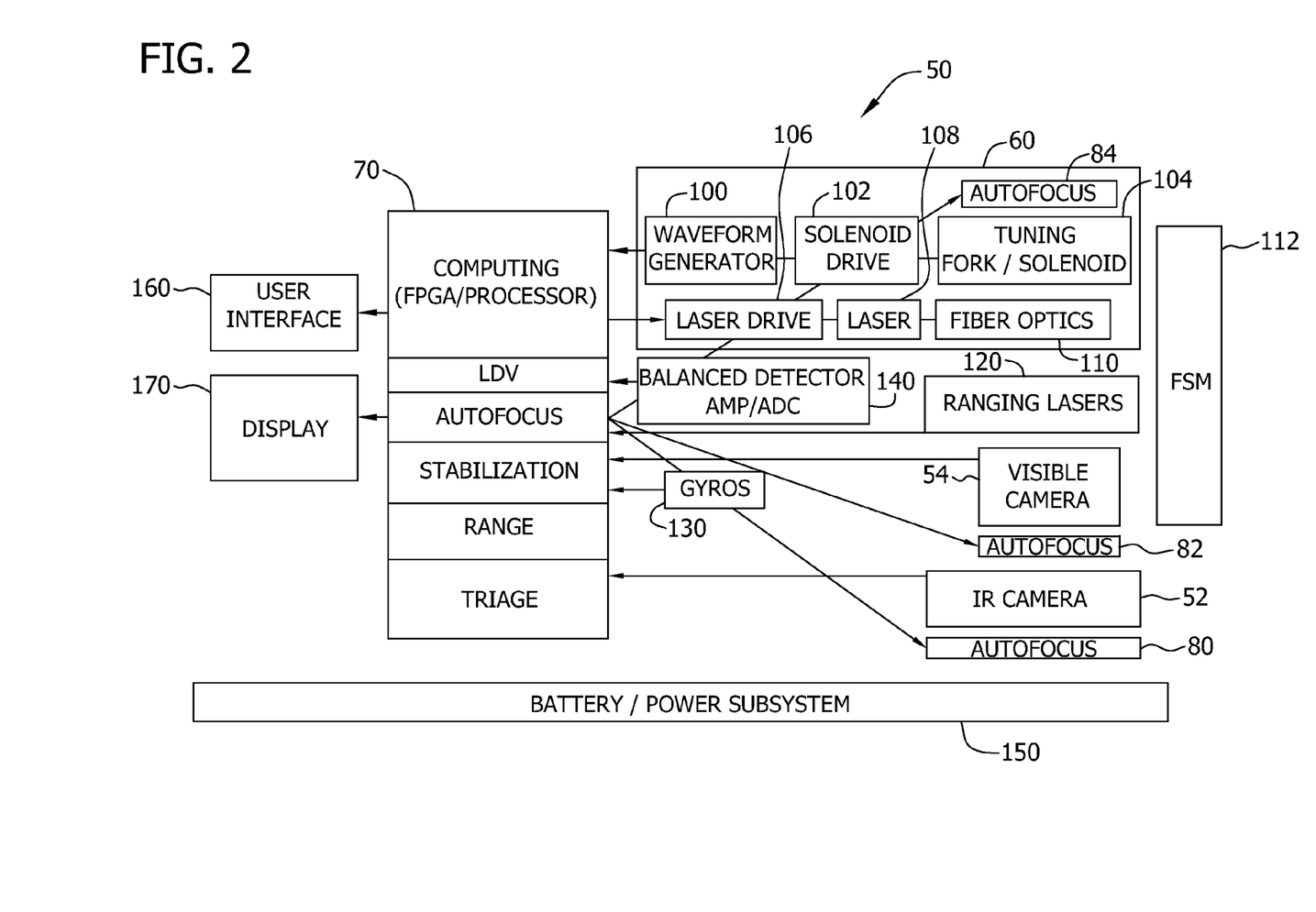
FIG. 2 is a block diagram of a non-contact biometric sensing device.

FIG. 2 is a block diagram of one embodiment of non-contact biometric sensing device 50. Device 50 combines an infrared camera 52, a visible camera 54 and a laser doppler vibrometer sensor 60. In order to operate in a handheld mode, the non-contact biometric sensing device 50 includes a processing device 70 which includes programming that operates to remove the motion of the user (first responder 10). In order to operate over a number of ranges, the non-contact biometric sensing device 50 includes autofocus methods programmed into the processing device 70 for the optical sensors. In the illustrated embodiment, there is an autofocus device 80 associated with the infrared camera 52, an autofocus device 82 associated with the visible camera 54, and an autofocus device 84 associated with the laser doppler vibrometer sensor 60. In addition to the autofocus device 84, laser doppler vibrometer sensor 60 includes a waveform generator 100, a solenoid drive 102, a tuning fork/solenoid 104, a laser driver 106, a laser 108 and associated fiber optics 110. A two-axis fine steering mirror 112 is included in embodiments of non-contact biometric sensing device 50 to stabilize laser beams emanating from and received by laser doppler vibrometer sensor 60.

In alternative embodiments, additional sensors are integrated into non-contact biometric sensing device 50 including ranging lasers 120, gyroscopes 130, and a detector amplifier/ADC 140 (analog-to-digital converter). Fine steering mirror 112 may also be utilized to stabilize laser beams emanating from and received by ranging lasers 120. Ranging lasers 120 provide visible laser guide beams which provide an indication for the user of where the sensors of device 50 are pointed. For example, if the visible laser beams are impinging person 20 (shown in FIG. 1) the user 10 knows that the other sensors (e.g., visible camera 54, IR camera 52, and laser doppler vibrometer sensor 60 are also directed to person 20. In certain embodiments, gyroscopes 130 are MEMS gyroscopes.

In embodiments, visible camera 54 is utilized for platform motion detection and processing device 70 (along with an algorithm running thereon) uses the information from visible camera 54 to remove the effects of motion of user 10 from the readings received from the other sensors. Similarly, gyroscope 130 is utilized to remove the hand motion associated with a user 10. In embodiments, and as described within the following paragraphs, functions included within non-contact biometric sensing device 50 include a linear motion detector, display, control buttons, an embedded computer, a field programmable gate array and associated firmware implementation of motion estimation algorithms, mirror controls, and sensor interfaces.

Non-contact biometric sensing device 50 further includes a battery/power subsystem 150, a user interface 160 and a user display 170. The battery/power subsystem 150 provides power to the other components of the device 50. The user interface 160 is communicatively coupled to the processing device 70 such that the programming stored therein can react to user input. The user display 170 is communicatively coupled to the processing device 70 such that information from the sensors described herein may be presented to the first responder 10.

As further described herein, device 50 enables standoff use, and also allows use by personnel wearing personal protective equipment, which hampers triage by direct contact methods. Device 50 measures mechanical motion, and measures temperature distribution, without contact at ranges of about five feet to about forty feet. Signals from the various sensors are processed by the processing device 70 to extract pulse rate, measure a breathing rate, and generate a map of temperature distribution on the human skin. These measurements indicate physical condition as calibrated with the measurements of physical condition by other contact methods such as strain belts, EKG and temperature probes.

Figure 3:
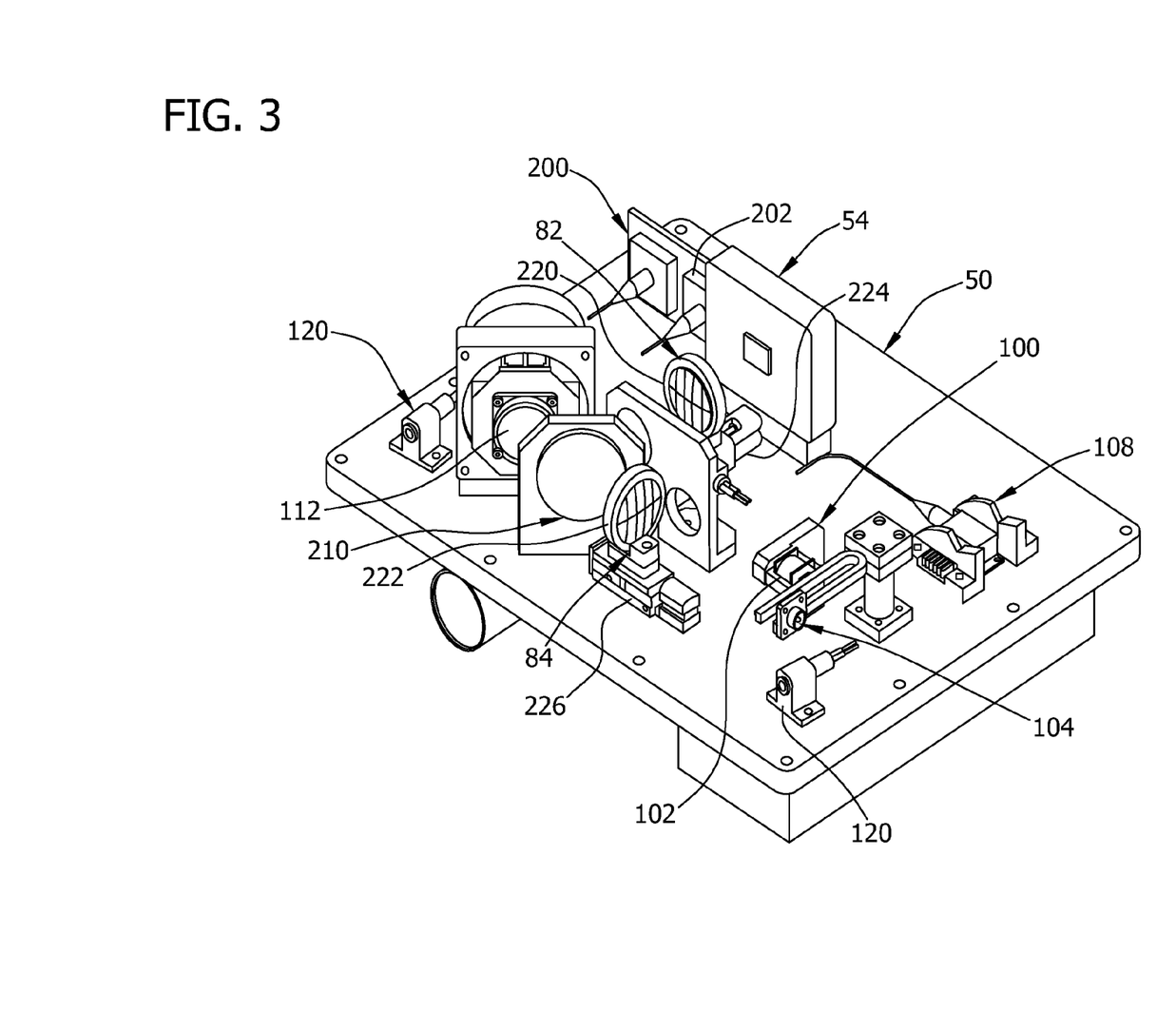
FIG. 3 is a top isometric view of the non-contact biometric sensing device of FIG. 2.

Turning now to FIG. 3, a top isometric view of non-contact biometric sensing device 50 is provided. Components that were described with respect to FIG. 2 are shown in FIG. 3 using the same reference numerals. Additionally, FIG. 3 illustrates two visible laser drivers 200 and 202 that are associated with the ranging lasers 120. An optical splitter 210 allows the wavelength of light associated with the laser doppler vibrometer sensor 60, from auto focus 84 to pass through to fine steering mirror 112. In the illustrated embodiment, the lenses 220 and 222 associated with autofocus devices 80 (not shown in FIG. 3), 82, and 84 respectively include a linear translator 224, 226 which moves the respective lens 220, 222 to accomplish the focusing function.

Figure 4:
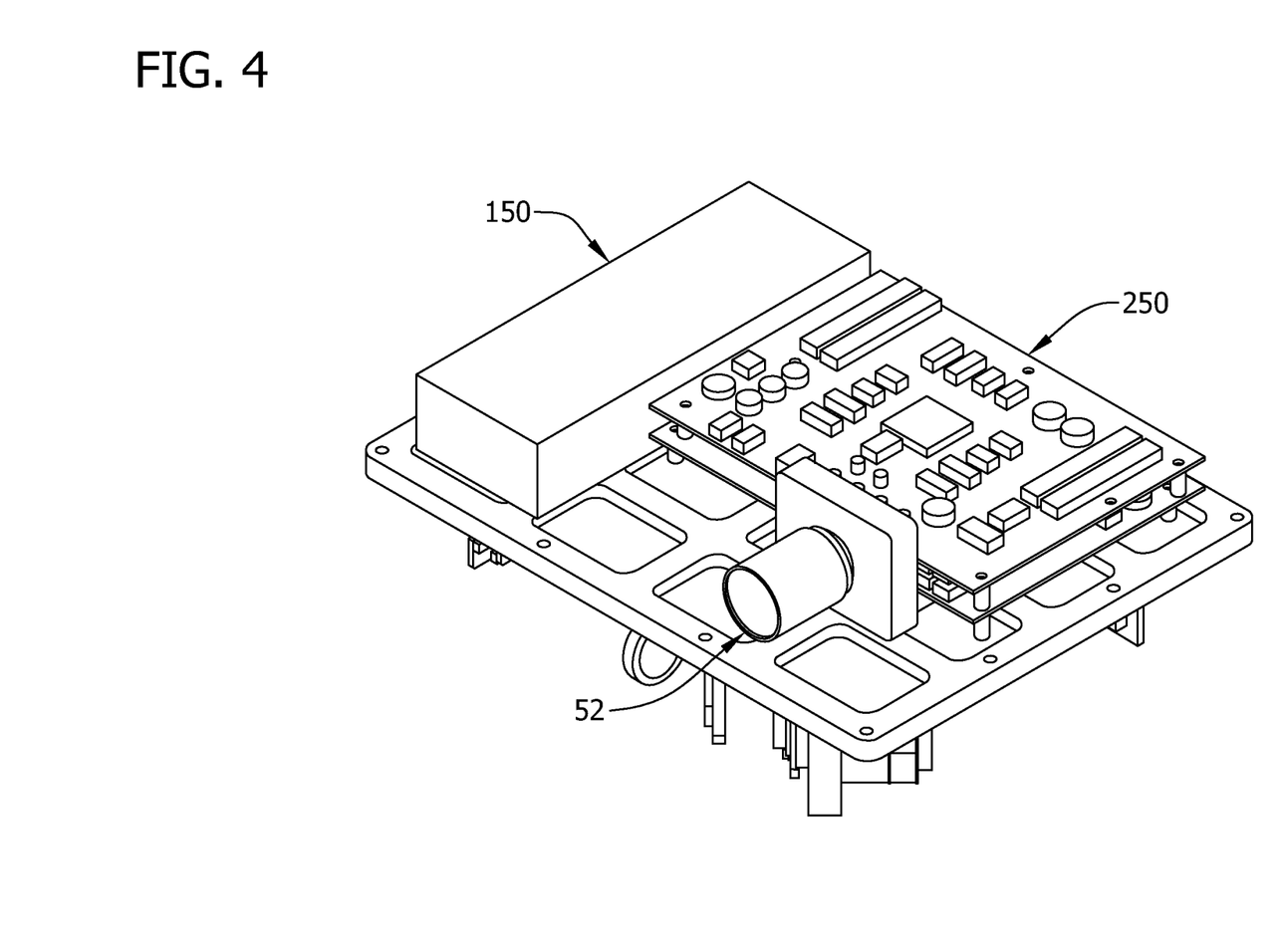
FIG. 4 is bottom isometric view of the non-contact biometric sensing device of FIG. 2.

FIG. 4 is a bottom isometric view of non-contact biometric sensing device 50 which illustrates the above described IR camera 52, battery/power subsystem 150 and printed circuit boards 250 which house the processing device 70 (not shown in FIG. 4 as well as supporting circuits for user interface 160 and display 170. In embodiments, an autofocus function is added to the IR camera 52, as shown in FIG. 2. For clarity, the autofocus function is not shown in FIG. 4 though in practice such a function is similar to 82 and 84 shown in FIG. 3 and in embodiments utilizes a linear translator.

Figure 5:
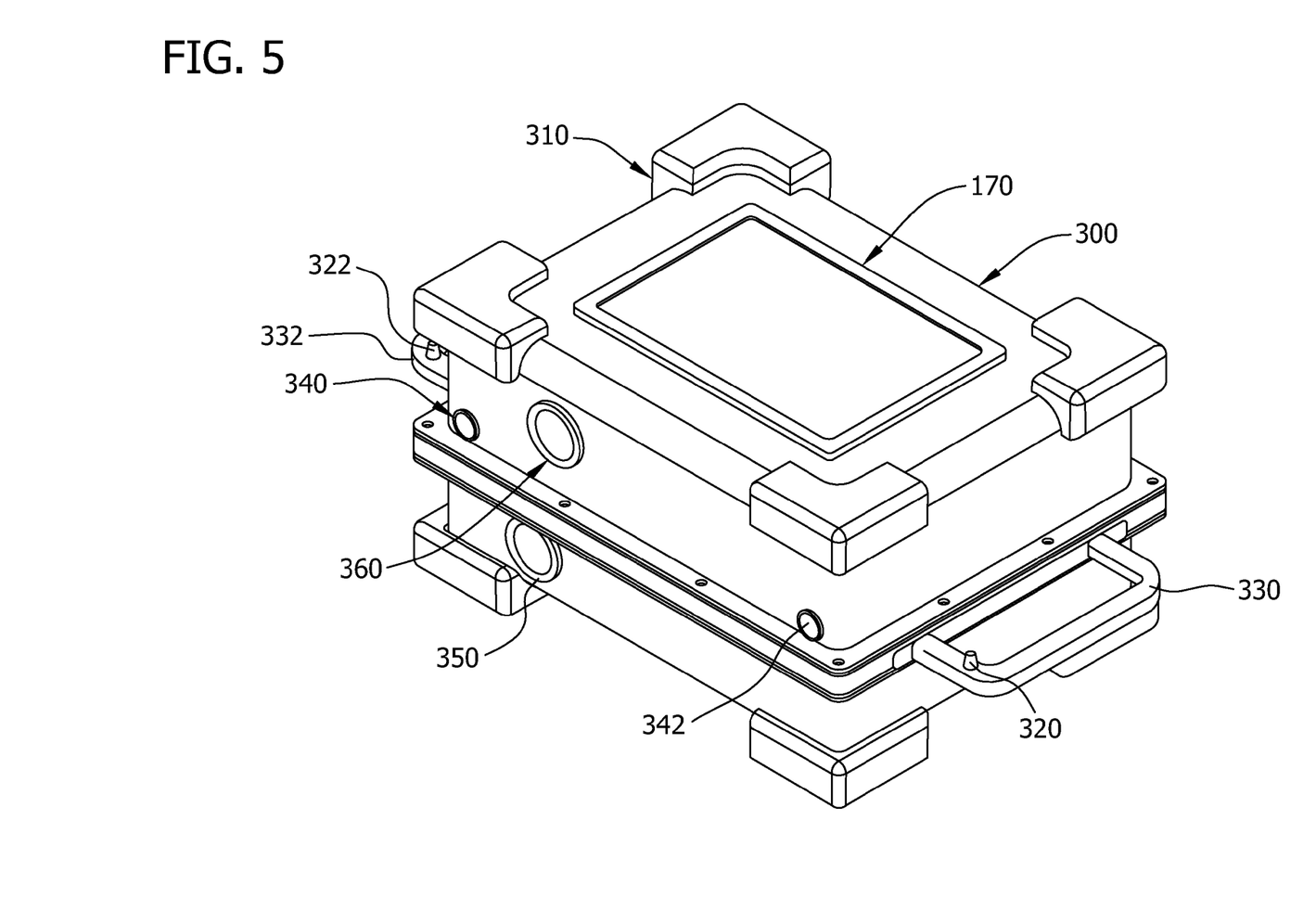
FIG. 5 is a top isometric view of an assembled non-contact biometric sensing device within a chassis.

FIG. 5 is a top isometric view of an assembled non-contact biometric sensing device 50 which includes a chassis 300 further including a plurality of shock and vibration isolating bumpers 310 mounted on corners of chassis 300. Also shown in FIG. 5 are the display 170 and buttons 320 and 322 on handles 330 and 332 of chassis. Buttons 320 and 322 make up at least a portion of user interface 160. Windows 340 and 342 for the ranging lasers 120 are shown as well as windows 350 and 360 for the infrared camera 52 and the visible camera 54.

As mentioned above, the above described system is operable for standoff measurement of biometric signals and is contemplated to function, at least in part, as a standoff triage device for civilian first responders and military first responders. To provide such functionality, the visible light from the ranging lasers 120 is utilized by the visible camera 54 to provide data that can be utilized by the processing device 70 to calculate an auto focus value for operation of the infrared camera 52 and the laser doppler vibrometer sensor 60. Specifically, the visible camera 54 sees the two laser beams from ranging lasers 120, measures how far apart the beams are at an impact point (e.g., on person 20 (shown in FIG. 1). The distance between the beams at the impact is utilized by the processing device 70 to determine a distance to the impact point and therefore control the autofocus function associated with the infrared camera 52, the visible camera 54, and the laser doppler vibrometer sensor 60.

In regard to operation of the laser doppler vibrometer sensor 60, it operates through the detection of reflected signals as sensed by detector/amplifier/ADC 140, which passes the detected signals onto the processing device 70 which is programmed to convert the received signals into velocities which is then passed to a triage algorithm. In embodiments, the laser doppler vibrometer sensor 60 has a data rate of about 800 Hz, a frequency resolution of 16 bits (−1 Hz in 100 kHz), a signal to noise resolution of 14 bits (10 in $10^6$), a mirror size of about one inch in diameter, a mirror quality of lambda/4, and is gold coated. The focus stage resolution of the laser doppler vibrometer sensor 60, in one embodiment, is 3.4 microns in 3 mm (0.2 Rayleigh range) and the ranging resolution is 0.04 in at 5 ft and two inches at 40 ft (0.1 Rayleigh range).

As is understood by those skilled in the art, non-contact biometric sensing device 50 is programmed with several operating modes, which are activated via the user interface 160 and executed by the processing device 70, which either accesses or includes a memory for storing the instructions utilized in operation of non-contact biometric sensing device 50. In embodiments, a sleep mode is included which operates to conserve battery power by turning the display 170 off, turning the various lasers off, and putting the processing device 70 into a low power mode. In a search mode, the display 170 is on, the lasers are on, a display of the long-wavelength infrared (LWIR) image provided by IR camera 52 is provided on display 170, and the beam stabilization afforded by the gyroscopes 130 and visible camera 54 for the laser doppler vibrometer sensor 60 is inactive and fixed in a neutral position.

Beam stability for one embodiment of the laser doppler vibrometer sensor 60 is about one centimeter. At 40 feet, this stability translates to about 0.047 degrees or about 820 micro radians. User hand jitter is stabilized up to about 20 Hz which implies a control loop bandwidth of about 2×, or 40 Hz, and a controller update rate of 10×, or 400 Hz. Beam pointing accuracy of the laser doppler vibrometer sensor 60 is about 1 to 1.5 centimeters.

Figure 6:
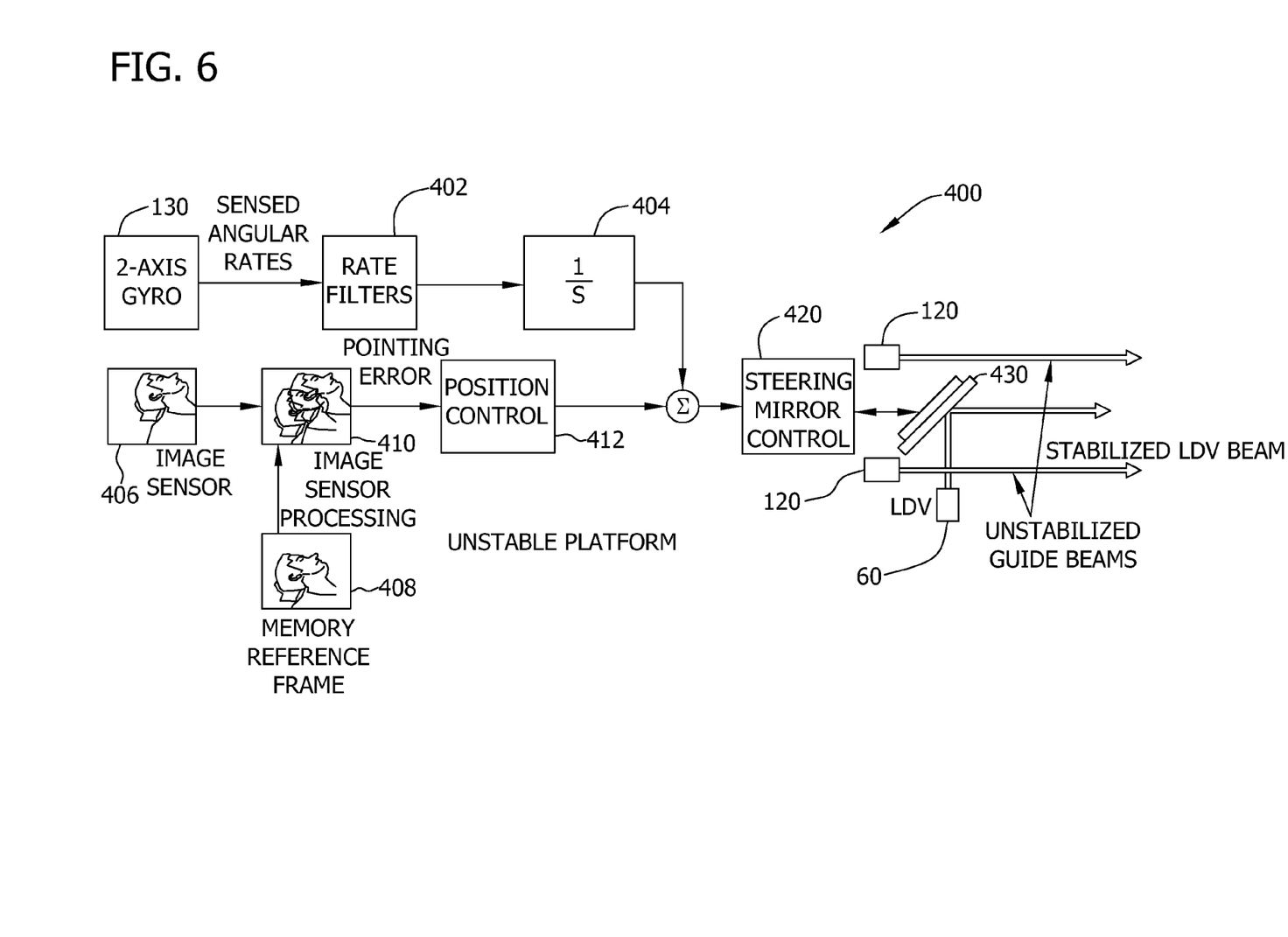
FIG. 6 is a block diagram of a pointing stabilization system.

FIG. 6 is a block diagram 400 of a pointing stabilization system and algorithm for device 50. Gyroscopes 130 provide sensing of two-axis angular rates that are associated with the user handling of the device 50. Rate filters 402 and integrator 404 within processing device 70 convert sensed rates to estimates of high-frequency platform angular pointing errors. In parallel, a sensed image 406 from visible camera 54 and a stored reference image 408 are subjected to an image sensor processing algorithm 410 to determine pointing errors due to low-frequency angular platform motion and two-DOF (depth of field) platform translations. A position control algorithm 412 determines steering mirror angles to compensate, and cancel out, such motion. Outputs of the rate filtering 402 and integrator 404 algorithms are combined with the outputs of the position control algorithm 412 and provided as data to the steering mirror control function 420 which continually adjusts positioning of the mirror 430 associated with laser doppler vibrometer sensor 60 to provide a stabilized laser beam. The gyroscopes 130 sense and outputs therefrom are utilized to cancel-out higher-frequency platform rotations. Concurrently, the camera-based motion-estimation algorithm compensates for DC-to-mid-frequency platform rotation and platform translation. The unstabilized guide beams from ranging lasers 120 aid the operator in keeping the steering mirror within range limits.

Figure 7:
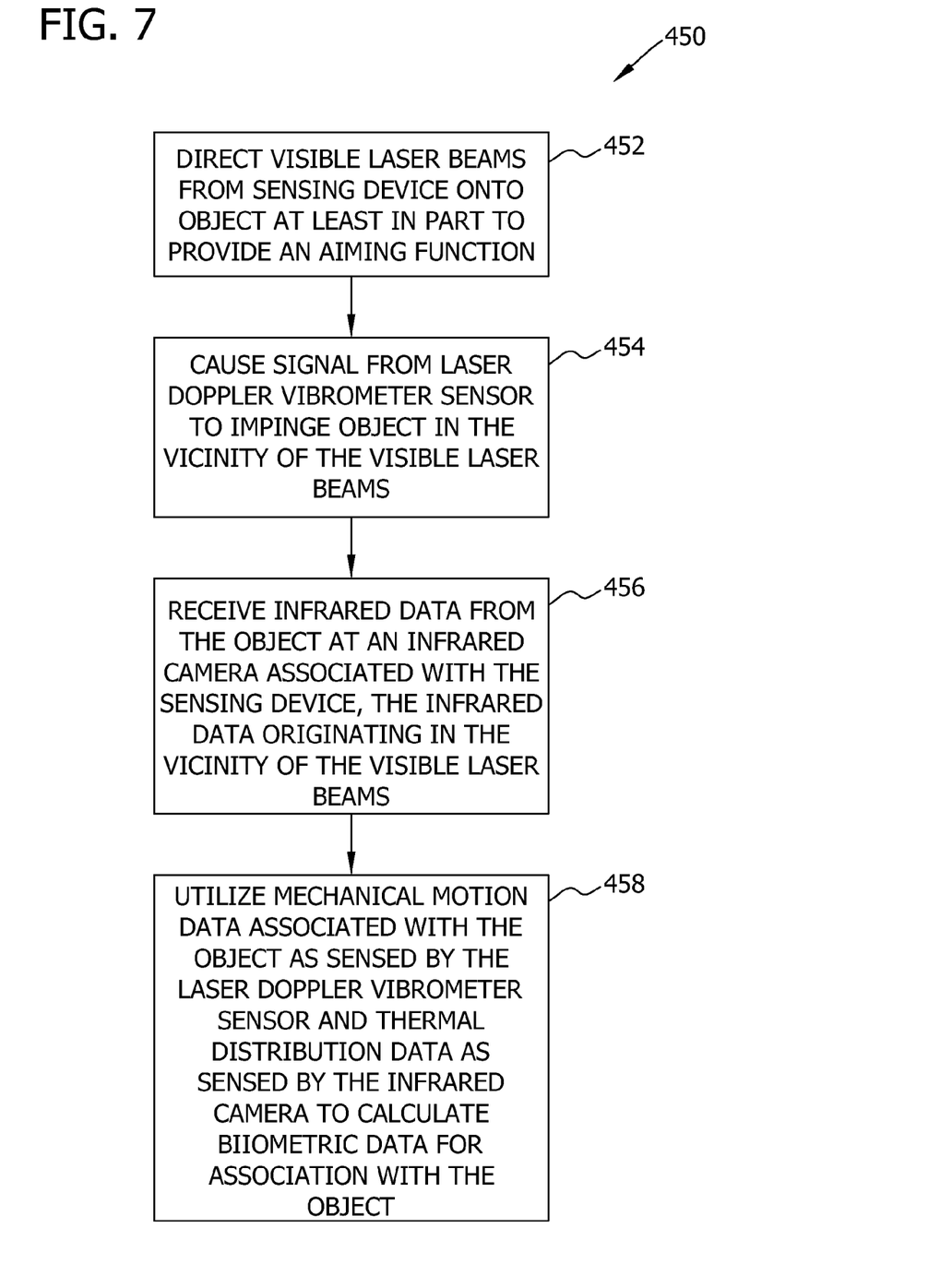
FIG. 7 is a flow diagram describing operation of the non-contact biometric sensing device of FIG. 2.

To further describe operation of non-contact biometric sensing device 50, FIG. 7 is a flow diagram 450 describing operation of the non-contact biometric sensing device 50 for the sensing of biometric parameters associated with an object. Initially, the user directs 452 a plurality of visible laser beams, emanating from sensing device 50, onto the object to provide an aiming function. Through user input or programming, a signal is caused 454 to be output from the laser doppler vibrometer sensor 60. The signal emanating from the laser doppler vibrometer sensor 60 from sensing device 50 thus impinges the object in the vicinity of the visible laser beams. Infrared data is received 456 from the object at the infrared camera 52 associated with the sensing device 50, where the infrared data is also in the vicinity of the visible laser beams. Mechanical motion data associated with the object as sensed by the laser doppler vibrometer sensor and thermal distribution data as sensed by the infrared camera is utilized 458 to calculate biometric data associated with the object.

In use, the user 10 aims the device 50 at person 20 using the guide beams from the visible ranging lasers 120, which are the dual, un-stabilized guide beams, and the measurement location for the infrared camera 54 and the laser doppler vibrometer sensor 60 is centered between guide beams. In one embodiment, the user 10 presses a "lock" button when guide beams are in the vicinity of the desired measurement location. An initial lock location could be several inches away from desired location, and the user 10 may utilize fine-adjust controls to move lock-location from initial to desired location. Alternatively, the user 10 presses a lock button repeatedly until initial lock is close enough to the desired measurement location. The user 10 holds the un-stabilized guide beams in the vicinity of the area being measured during measurement for a period of time due to limited range on the fast steering mirror 112.

In an autofocus mode, a range to the target is measured, based on the beams provided by the visible ranging lasers 120, focus is set, beam stabilization for the laser doppler vibrometer sensor 60 is active, and a final LWIR image is acquired. In addition, a patient identifier is incremented. In a first acquire mode, the signal from laser doppler vibrometer sensor 60 is acquired and displayed, acquisition of the signal is the first attempt to detect a pulse or other signs of life of person 20. In a second acquire mode, acquisition and display of the laser doppler vibrometer sensor 60 signal is continued, and an attempt to detect respiration as well as the processing and display of a pulse rate is begun. In a third acquire mode, acquisition and display of the laser doppler vibrometer sensor 60 signal is continued, and an attempt to process and display respiration rate is made. In an analyze mode, beam stabilization for the laser doppler vibrometer sensor 60 signal is inactive, while the processing device continues to analyze collected data to present a diagnosis. A diagnostic mode is used to capture and store raw data for troubleshooting. One or more of the buttons 320 and 322 are used as an on/off switch and as a switch to change between the above described operations modes or to select a body part which is being analyzed (e.g., carotid, chest, other). In embodiments, LEDs may be incorporated to provide an indication of which mode the device 50 is operating in.

As described herein, the device 50 is utilized to perform a triage function, typically to be used by first responders at the scene of an incident or accident. The triage function can be broken down to establish a timeline hierarchy of analysis. Specifically, the first 3-5 seconds is utilized to detect primitive signs of life, including, displaying of mechanical motion against time, displaying the image as provided by IR camera 52 as a colorized map of absolute temperature, and detecting a pulse, as well as including an indication of confidence and/or signal quality. At 10-20 seconds, respiration mechanical motion is detected while the pulse rate is processed and displayed, including an indication of confidence and/or signal quality. At 30-60 seconds respiration rate is processed and displayed, pulse quality is evaluated, and if possible, a diagnosis is presented and/or a quantitative measure of patient health (i.e. 0=dead . . . 100=healthy) is provided, also including an indication of confidence and/or signal quality.

FIG. 7 is a flow diagram 500 of a data pre-processing stage for a pulse algorithm. A velocity signal is read 502 by the laser doppler vibrometer sensor 60 which is sampled 504 by the processing device 70, through detector/amplifier 140, and despeckled to create 506 new output channels including a heart sound channel 510, a maximum velocity peak detection channel 512, a landmark detection/measurement channel 514, an artifact auto-detection channel 516 and a respiration channel 518. These channels are passed through various filters and other processing and the results are written 520 to a file.

Figure 8:
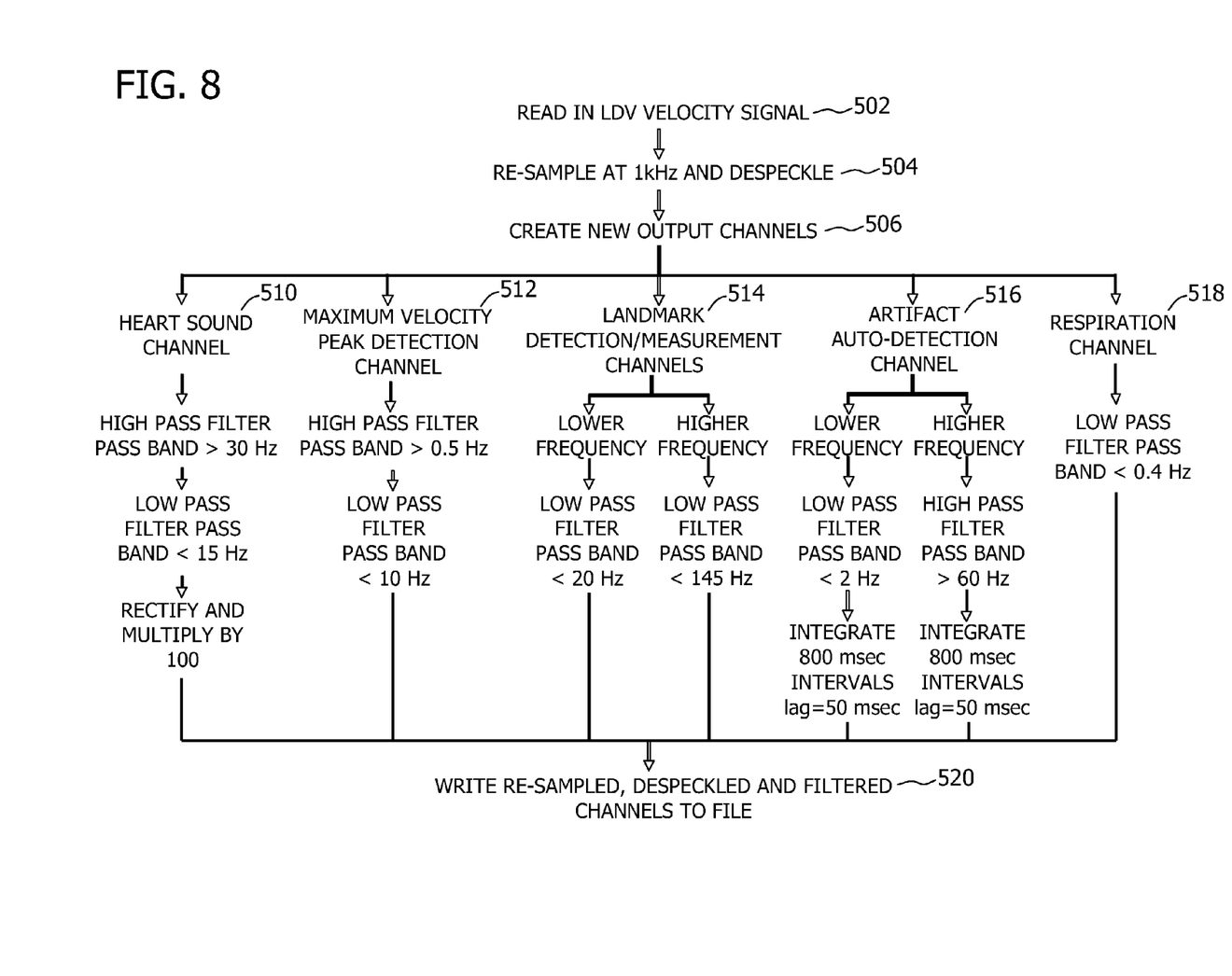
FIG. 8 is a flow diagram of a data pre-processing stage for a pulse algorithm.

FIG. 8 is a flow diagram 550 of a model calibration stage for a pulse algorithm. In one embodiment, 15 seconds of data from a pre-processed file (see FIG. 7) is read 552 and maximum likelihood heartbeats are identified 554 using, for example, generic models from which individualized models are created 556. The models include, in one embodiment, a heart sounds model 560, a maximum velocity peak detection model 562, a landmark detection/measurement model 564, and an artifact auto-detection model 566. In regard to the landmark detection/measurement model 564, if the correlation between a current higher frequency measurement model and the model from the previous 15 second input exceeds 570 a criterion, consecutive models are averaged 572 and stored. If the criterion is not exceeded 570, another 15 seconds of data is read 552 and the process continues.

Figure 9:
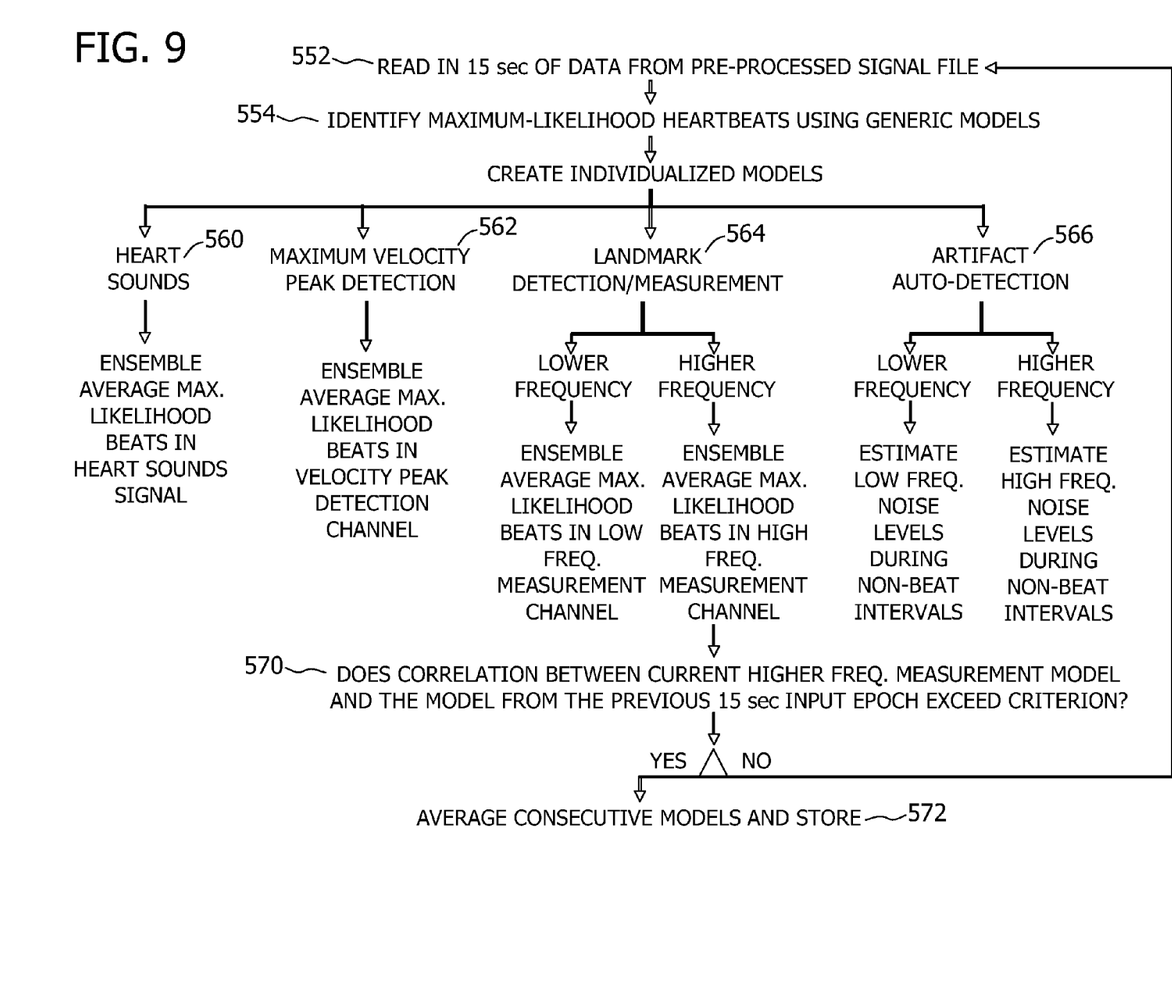
FIG. 9 is a flow diagram of a model calibration stage for a pulse algorithm.

FIG. 9 is a flow diagram 600 of an initial detection/quantification stage for a pulse algorithm. Initially, 25 seconds of data is read 602 in from a pre-processed signal file (see FIG. 7), in one embodiment, with a three second overlap with the preceding epoch. "Candidate" beats are identified 604 using cross-correlation between heart sounds input channel and heart sounds model, for example, when both are down-sampled to 20 Hz. Appropriate maximum velocity peaks and extract epochs are identified 606 if an amplitude of a maximum velocity peak lies within expected values. Next, extracted epochs are labeled 608 as "detected beats" if correlation with the maximum velocity detection model exceeds a criterion. Lower and higher frequency landmark detection epochs are extracted 610 and single beat landmarks (in higher and lower frequency signals) are detected 612 and quantified. Models are dynamically updated 614, and epoch points exceeding low and high frequency "noise" criteria are identified 616. If the end of the input file been reached 618, write 620 all detections and measurements to and output file. Otherwise read 602 another 25 seconds of data.

Figure 10:
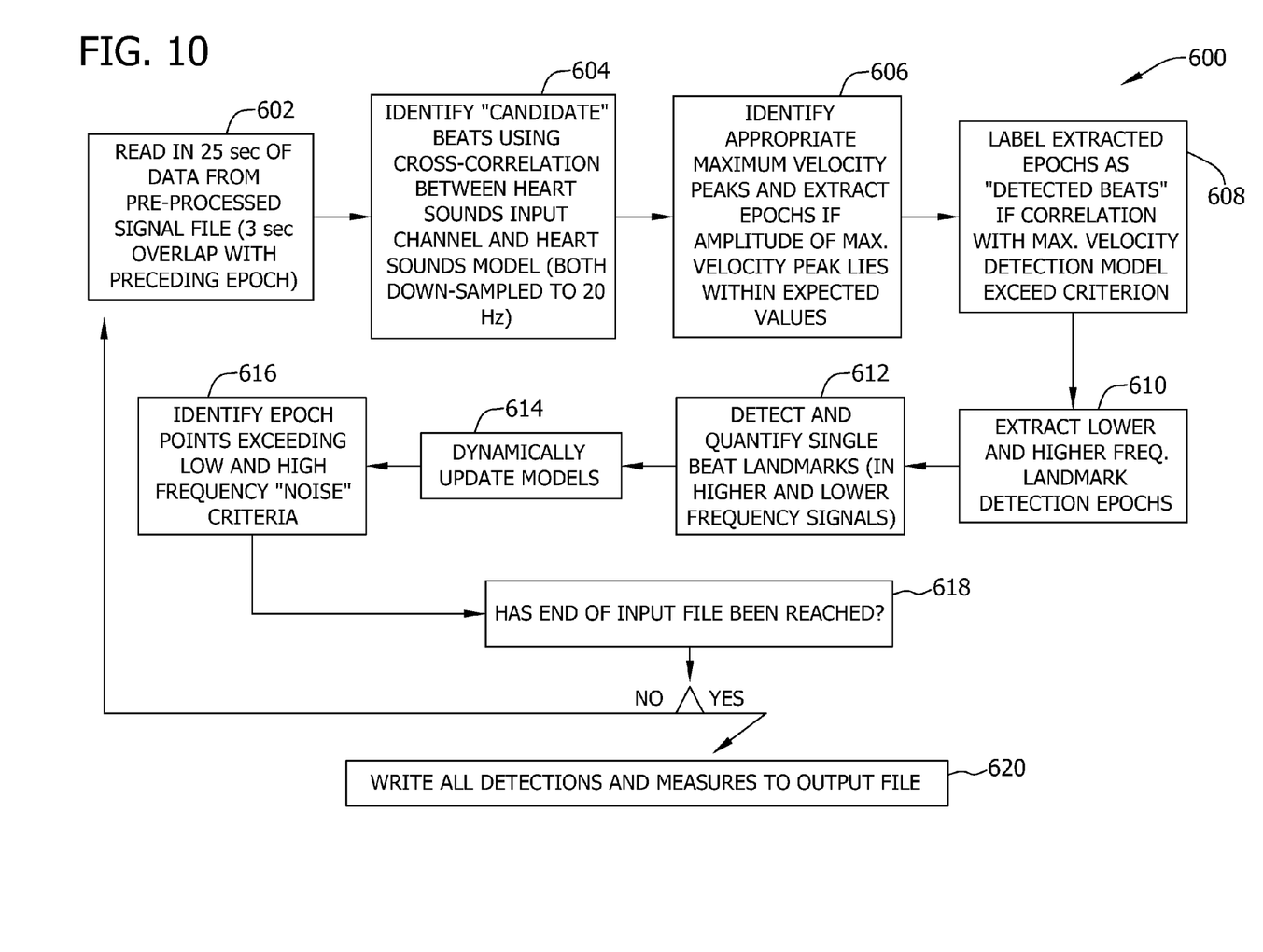
FIG. 10 is a flow diagram of an initial detection/quantification stage for a pulse algorithm.
Figure 11:
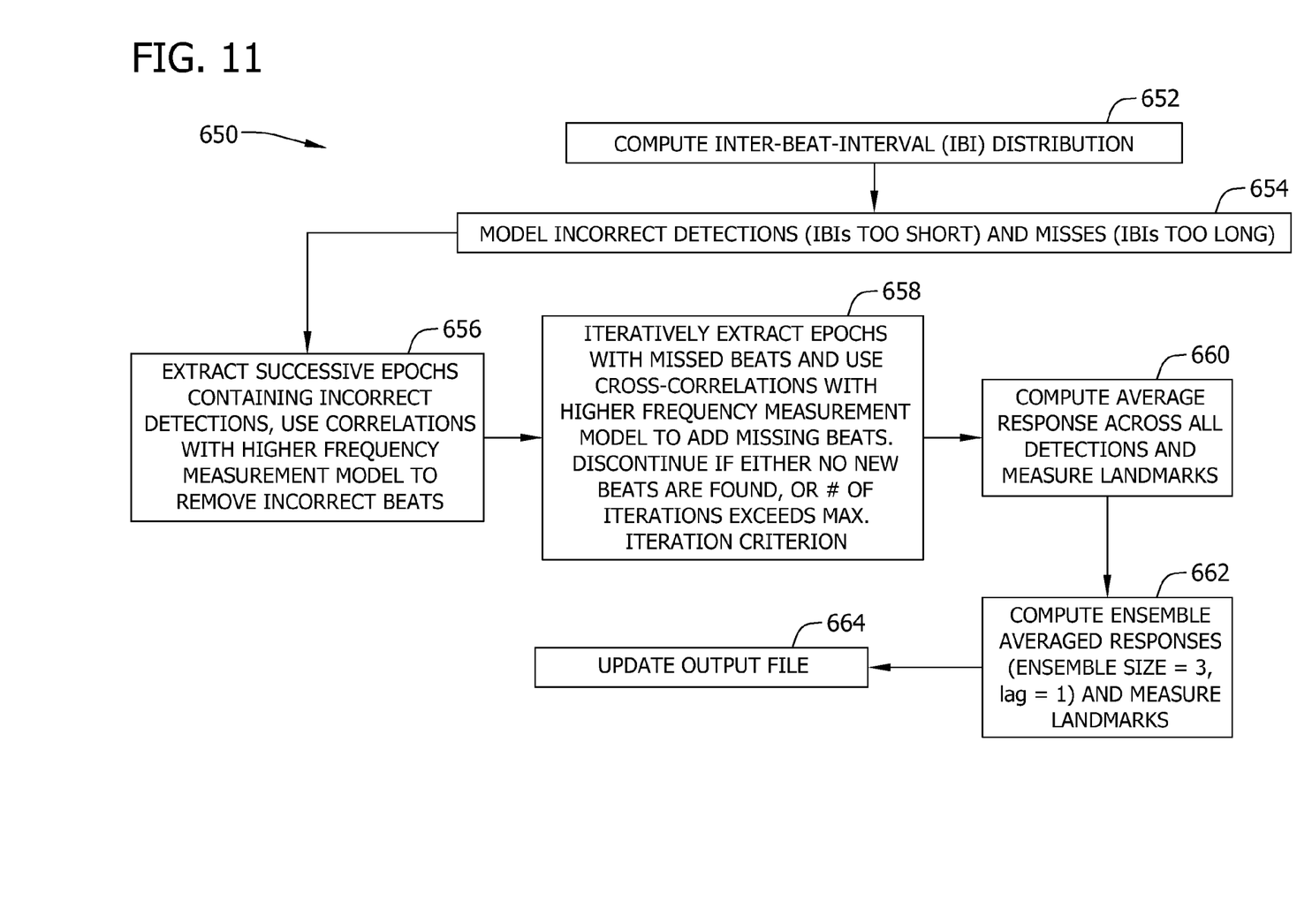
FIG. 11 is a flow diagram of a post-detection processing stage for a pulse algorithm.

FIG. 10 is a flow diagram 650 of a post-detection processing stage for a pulse algorithm. Initially, an Inter-Beat-Interval (IBI) distribution is computed 652 and incorrect detections (IBIs too short) and misses (IBIs too long) are modeled 654. Successive epochs containing incorrect detections are extracted 656, and correlations with higher frequency measurement model are used to remove incorrect beats. Epochs with missed beats are iteratively extracted 658 and cross-correlations with higher frequency measurement models are used to add missing beats. Discontinue if either no new beats are found, or if the number of iterations exceeds a maximum iteration criterion. An average response across all detections and measure landmarks is computed 660 and ensemble averaged responses (ensemble size=3, lag=1) are computed 662. Landmarks are measured and an output file is updated 664.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A non-contact biometric sensing device comprising:
   a processing device;
   a user interface communicatively coupled to said processing device;
   a display communicatively coupled to said processing device;
   a laser doppler vibrometer sensor communicatively coupled to said processing device;
   an infrared camera communicatively coupled to said processing device, said processing device programmed to utilize mechanical motion data received from said laser doppler vibrometer sensor and thermal distributions data from said infrared camera to calculate biometric data, when signals originating from said laser doppler vibrometer sensor and said infrared camera are reflected back towards said device from a target, wherein the biometric data includes at least two of a pulse rate, a respiration rate, and a map of temperature distribution on the target, said processing device further programmed to generate, based on the biometric data, at least one of a potential diagnosis for the target and a quantitative measure of target health represented as a score within a predefined range of scores; and
   a visible camera communicatively coupled to said processing device, said processing device programmed to utilize data received from said visible camera to remove hand motion associated with a user of said sensing device from the data received from said laser doppler vibrometer sensor and said infrared camera.

2. The non-contact biometric sensing device according to claim 1 further comprising a plurality of ranging lasers each configured to emanate a visible beam for use as an aiming device for said sensing device.

3. The non-contact biometric sensing device according to claim 2 wherein signals from said laser doppler vibrometer sensor and said infrared camera are configured to emanate from a position between the visible beams of said ranging lasers.

4. The non-contact biometric sensing device according to claim 2 wherein to utilize data received from said visible camera, said processing device is programmed to utilize data received from said visible camera, including the tracking of beams from said ranging lasers, to remove the hand motion associated with a user of said sensing device from the data received from said laser doppler vibrometer sensor and said infrared camera.

5. The non-contact biometric sensing device according to claim 4 wherein said processing device is programmed to determine a change in the X and Y directions between an image sensed by said visible camera and a stored reference image previously sensed by said visible camera, said processing device further programmed to continually adjust positioning of mirrors associated with said laser doppler vibrometer sensor, based on the changes in the X and Y directions, to provide a stabilized laser beam from said laser doppler vibrometer sensor.

6. The non-contact biometric sensing device according to claim 1 further comprising at least one gyroscope communicatively coupled to said processing device, said processing device programmed to utilize data received from said gyroscopes to remove the hand motion associated with a user of said sensing device from the data received from said laser doppler vibrometer sensor and said infrared camera.

7. The non-contact biometric sensing device according to claim 6 wherein said gyroscopes are configured to output a pitch rate and a yaw rate that is associated with user handling of said sensing device, said processing device programmed with an algorithm which uses sensed angular rate data to estimate higher-frequency angular pointing errors and said processing device is programmed to continually adjust positioning of mirrors associated with said laser doppler vibrometer sensor, to remove the hand motion associated with a user of said sensing device.

8. The non-contact biometric sensing device according to claim 2 further comprising a gyroscope communicatively coupled to said processing device, said processing device programmed to utilize data from said gyroscope to cancel-out higher frequency platform rotations sensed by said gyroscope, said processing device programmed to utilize data from said visible camera to compensate for lower frequency rotations and X/Y translations.

9. The non-contact biometric sensing device according to claim 2 wherein said processing device is programmed to utilize a distance, at a target location, between the laser beams emanating from said ranging lasers and sensed by said visible camera to determine a range to the target.

10. The non-contact biometric sensing device according to claim 1 further comprising:
a plurality of ranging lasers each configured to emanate a visible beam for use as an aiming device for said sensing device; and
a visible camera communicatively coupled to said processing device, said laser doppler vibrometer sensor, said infrared camera, and said visible camera comprising lenses associated with an autofocus function, said processing device programmed with the autofocus function, the autofocus function based on a range to a target as measured using the visible beams from said ranging lasers.

11. A non-contact biometric sensing device comprising:
a plurality of ranging lasers each configured to emanate a visible laser beam, the ranging lasers oriented such that the visible laser beams converge at a point distant from said sensing device, the laser beams operable in aiming said sensing device at a target object;
a laser doppler vibrometer sensor configured to sense mechanical motion associated with the target object;
an infrared camera configured to sense thermal distribution data associated with the target object;
a visible light camera operable to obtain an image of the target object that includes the visible laser beams, said sensing device programmed to determine a distance to the target object based upon a distance between the visible beams and calculate biometric data based on at least one of the mechanical motion sensed by said laser doppler vibrometer sensor and the thermal distribution data sensed by said infrared camera, the biometric data including at least two of a pulse rate, a respiration rate, and a map of temperature distribution on the target, said sensing device further operable to use the determined distance to the target to focus said laser doppler vibrometer sensor, said infrared camera and said visible light camera on the target object, said sensing device further operable to generate, based on the biometric data, at least one of a potential diagnosis for the target object and a quantitative measure of target health represented as a score within a predefined range of scores, said sensing device operable to utilize data received from said visible light camera to remove hand motion associated with a user of said sensing device from the data received from said laser doppler vibrometer sensor and said infrared camera; and
a portable housing containing said plurality of ranging lasers, said laser doppler vibrometer sensor, said infrared camera, and said visible light camera, said portable housing configured for handheld use.

12. The non-contact biometric sensing device according to claim 11 further comprising a gyroscope, said sensing device programmed to utilize data from said gyroscope and image data from said visible light camera to remove effects of movement of said sensing device from data associated with said laser doppler vibrometer sensor and said infrared camera.

* * * * *